United States Patent
Norén et al.

(10) Patent No.: US 7,569,020 B2
(45) Date of Patent: Aug. 4, 2009

(54) METHOD FOR EXTRACTING TIMING PARAMETERS USING A CARDIO-MECHANICAL SENSOR

(75) Inventors: Kjell Norén, Solna (SE); Nils Holmström, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 396 days.

(21) Appl. No.: 11/455,518

(22) Filed: Jun. 19, 2006

(65) Prior Publication Data
US 2007/0293771 A1    Dec. 20, 2007

(51) Int. Cl.
*A61B 5/026*    (2006.01)
(52) U.S. Cl. .................................. 600/526
(58) Field of Classification Search ............ 600/526
See application file for complete search history.

(56) References Cited

U.S. PATENT DOCUMENTS

| | | | | |
|---|---|---|---|---|
| 4,289,141 A | * | 9/1981 | Cormier | 600/526 |
| 4,549,552 A | * | 10/1985 | Groch et al. | 600/513 |
| 4,649,930 A | * | 3/1987 | Groch et al. | 600/508 |
| 4,719,921 A | | 1/1988 | Chirife | |
| 4,865,036 A | * | 9/1989 | Chirife | 607/14 |
| 5,154,171 A | * | 10/1992 | Chirife | 607/24 |
| 5,168,869 A | | 12/1992 | Chirife | |
| 5,443,074 A | * | 8/1995 | Roelandt et al. | 600/526 |
| 5,447,523 A | | 9/1995 | Schaldach | |
| 5,450,850 A | * | 9/1995 | Iinuma | 600/455 |
| 5,514,171 A | | 5/1996 | Hoegnelid et al. | |
| 5,549,650 A | | 8/1996 | Bornzin et al. | |
| 5,743,268 A | * | 4/1998 | Kabal | 600/526 |
| 6,044,297 A | | 3/2000 | Sheldon et al. | |
| 6,602,201 B1 | * | 8/2003 | Hepp et al. | 600/526 |
| 6,666,826 B2 | | 12/2003 | Salo et al. | |
| 6,934,586 B2 | | 8/2005 | Struble et al. | |
| 6,952,612 B1 | * | 10/2005 | Lu | 607/30 |
| 6,978,184 B1 | * | 12/2005 | Marcus et al. | 607/120 |
| 6,993,379 B1 | | 1/2006 | Kroll et al. | |
| 7,003,348 B1 | | 2/2006 | Brewer et al. | |

(Continued)

FOREIGN PATENT DOCUMENTS

EP    0 824 935    2/1998

(Continued)

OTHER PUBLICATIONS

"Non-Invasive Ejection Fraction Monitoring: A Comparison of the Impedance Method to the Radionuclide Cardiography," Hanna et al, Anesthesiology, vol. 69, No. 34, Sep. 1989 (p. A308).

(Continued)

*Primary Examiner*—Angela D Sykes
*Assistant Examiner*—Amanda Patton
(74) *Attorney, Agent, or Firm*—Schiff Hardin LLP (57) ABSTRACT

In a method and apparatus for measuring the ejection fraction in a mammalian heart, the opening and closing of a heart valve is sensed with an implanted sensor, and a pre-ejection period is measured as a function of the sensed opening and closing of the heart valve. The ventricular ejection time also is measured, and the ejection fraction is determined as a function of the measured pre-ejection period and the ejection time.

20 Claims, 6 Drawing Sheets

U.S. PATENT DOCUMENTS

| | | | |
|---|---|---|---|
| 7,190,994 B2 * | 3/2007 | Mohler et al. | 600/514 |
| 2003/0199934 A1 | 10/2003 | Struble et al. | |
| 2004/0138571 A1 | 7/2004 | Salo et al. | |
| 2005/0240087 A1 * | 10/2005 | Keenan et al. | 600/301 |
| 2006/0095085 A1 * | 5/2006 | Marcus et al. | 607/17 |

FOREIGN PATENT DOCUMENTS

| | | |
|---|---|---|
| WO | WO 02/34130 | 5/2002 |
| WO | WO 03/089057 | 10/2003 |

OTHER PUBLICATIONS

"The Relationship of Systolic Time Intervals to Ejection Fraction in Patients with Cardiac Disease," Garrad et al, Circulation, vol. 42, 1970 (pp. 455-462).

"Measurement of Ejection Fraction by Bioimpedance," Capan et al, Critical Care Medicine, vol. 15 (Apr. 1987) p. 402.

* cited by examiner

METHOD FOR EXTRACTING TIMING PARAMETERS USING A CARDIO-MECHANICAL SENSOR

BACKGROUND OF THE INVENTION

1. Field of the Invention

The present invention relates to systems and methods for conditioning signals obtained from a sensor preferably located in a coronary vessel.

2. Description of the Prior Art

The assessment of cardiac function is a common problem in the evaluation of patients. The gold standard is the measurement of the ejection fraction (EF or LVEF) by echocardiography. The ejection fraction is the amount of blood pumped out of a ventricle during each heart beat. The EF evaluates how well the heart is pumping. The normal value is 65 percent (with a typical range being 50-70 percent). Lower values indicate ventricular dysfunction. The normal left ventricle has an average volume of 100 ml. Each heart beat ejects approximately 70 ml, which results in an EF≈70%. Noninvasive measurement of ejection fraction by echocardiography requires expertise and (expensive) equipment that is not always available. Further the patient must travel to the hospital.

A similar measurement of cardiac contractility, the ability of the myocardial muscle to shorten itself, is of interest to monitor continuously without advanced technical support. Invasive measures of myocardial contractility are performed by left heart catheterization, angiography and radionuclide ventriculography. None of the techniques described above allows for trending when the patient is at home.

It has been known by clinicians that there is a direct relationship between the systolic time intervals (particularly PEP/LVET, i.e., Pre-Ejection Period/Left Ventricular Ejection Time) and the left ventricular ejection fraction. (See, for instance: Hanna L, et al., "Non-invasive ejection fraction monitoring: A comparison of the impedance method to the radionuclide cardiography," Anesth 1989; 69: A308.)

The timing relation PEP/LVET=STR (Systolic Time Ratio) has been found to be inversely related to cardiac contractility. The normal value is 0.35. A higher value indicates impaired contractility. The ratio PEP/LVET was first used by Weissler more than 35 years ago to noninvasively calculate the cardiac ejection fraction (see Garrad C L Jr, Weissler A M, and Dodge H T, "The relationship of systolic time intervals to ejection fraction in patients with cardiac disease." Circulation 1970; 42: 455-462.)

The ejection fraction is determined by the Weissler method as follows:

$$EF=1.125-1.25*(PEP/LVET)$$

where EF=ejection fraction,
PEP=pre-ejection period, and
LVET=left ventricular ejection time.

Capan validated a similar method (Capan L V, Bernstein D P, Patel K P et al. "Measurement of ejection fraction by bioimpedance." Crit Med 1987; 15: 402.)

Ejection fraction is determined by the Capan method as follows:

$$EF=0.84-0.64*(PEP/LVET)$$

Tracing of timing parameters in the heart interval provides important clinical measures that otherwise has to done at the hospital. This can be done continuously by an implanted device. Continuous monitoring of cardiac function makes it possible to trace the outcome of given therapies, including implanted devices and drugs. The measured values can also be used to control the device stimulation therapy in a closed loop manner.

One scenario is to transfer the monitored parameters stored in the device to the hospital by Internet. Medical actions can then be taken if the cardiac parameters pass predetermined limits.

It would be of great benefit to the patient to be able to continuously measure the PEP and LVET in the implanted device. Similarly, trending of contractility and EF can be performed by using the relation PEP/LVET. Long time trending of EF is important as the EF value varies in both the short and long terms, from beat to beat, minute to minute, hour to hour, and day to day.

SUMMARY OF THE INVENTION

An object of the present invention is to provide a system and method for measuring and trending EF and providing the trend information to a clinician non-invasively. A further object is to provide such a system and method that allow trend values to be determined based on short term values.

The above object is achieved in accordance with the present invention by an apparatus and method for measuring ejection fraction in a mammalian heart wherein the opening and closing of a heart valve are detected with an implanted sensor, a pre-ejection period is measured as a function of the detected opening and closing of the heart valve is measured; ventricular ejection time is measured; and an ejection fraction is determined as a function of the measured pre-ejection period and ejection time.

DESCRIPTION OF THE PREFERRED EMBODIMENTS

The invention involves measuring pre-ejection period (PEP) and left ventricular ejection time (LVET) to determine the ejection fraction (EF) and to trend the data over time. This provides an advantageous monitoring of a patient's cardiac function in a minimally invasive manner with a minimum of disruption to the patient.

The invention achieves a robust detection of the opening and closing of the aortic valve of a heart chamber by processing the measured raw signal from an implanted sensor. It was found that a robust detection of the opening and closing of the aortic valve can be achieved by analyzing the signal energy (power) in a frequency range much higher than the heart rate.

The signal processing of the invention is insensitive to circadian signal morphology changes for a patient. In one embodiment of the invention, the time derivative of the raw signal rather than the raw signal itself is processed as the high frequency parts are enhanced in the time derivative.

A bandpass filter, approx 20-40 Hz, cuts out the (high) frequency range to be further analyzed. Squaring of the bandpass filtered output represents the instantaneous power in the frequency range. Smoothing of the instantaneous power then produces two characteristic peaks in the heart interval. The first peak, occurring within 30-150 ms from the electrical activation, has a larger amplitude then the second peak, occurring around the T-wave (200-500 ms). The first and second peaks can sometimes be split into several peaks. The time location relative to the electrical event constitutes the first or second peak.

The aortic valve opening is defined as the minimum point of the time derivative of the first peak; that is the maximum decrease rate in the signal power. The time difference from electrical activation to the minimum time derivative point gives the PEP. A time window synchronized with the electrical event defines the time interval to search for this minimum. The time derivative of the first peak is sometimes split up into several peaks. The preferred peak is the first minimum peak in a first time window.

The aortic valve closing is defined as the first maximum point of the time derivative of the second peak; that is the maximum increase rate in the signal power. The time difference electrical activation to the time derivative maximum point gives the EMS. A time window synchronized with the electrical event defines the time interval to search for this maximum. The time derivative of the second peak is sometimes split up into several peaks. The preferred peak is the first maximum peak in a second time window.

Knowing PEP and EMS, LVET can be calculated as EMS–PEP. This follows the contractility measure STR=PEP/LVET; and EF=Constant1−Constant2*STR.

EMS=electromechanical systole, which is the interval from the onset of the QRS complex on the electrocardiogram to the aortic component of the second heart sound; it is one of the systolic time intervals (q.v.), encompassing the left ventricular ejection time and the pre-ejection period, and is used to assess left ventricular performance.

Figure 1:
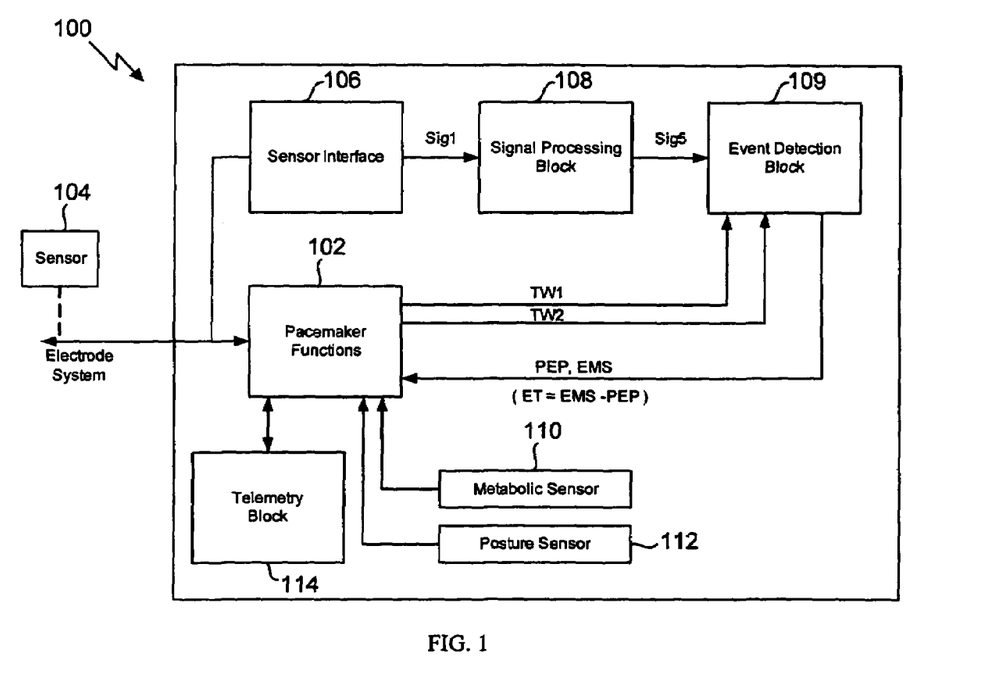
FIG. 1 is a schematic block diagram of an implantable cardiac device having an electrode system with a connected sensor, constructed and operating in accordance with the invention.

FIG. 1 is a schematic block diagram of a cardiac signal monitoring system 100. System 100 includes a pulse generator, such as a pacemaker or implantable cardiac device (ICD), 102, of the type described, for example, in U.S. Pat. No. 7,003,348, issued Feb. 21, 2006, titled "Monitoring cardiac geometry for diagnostics and therapy," the disclosure of which is incorporated herein in its entirety, as though set forth in full below. Pulse generator 102 contains a portion having pacemaker functions. In one embodiment, a sensor 104 is incorporated into a standard electrode array that is coupled to pulse generator 102. An electrode system typically includes electrodes for stimulating and sensing electrical events in the heart which are typically located in the right atrium, right ventricle and coronary veins. Epicardial electrode locations can also be used. Different stimulation modes ("pacing modalities") may be applied as therapy for the patient's heart problem. Specifically, coronary vein or epicardial electrode positions have the advantage of stimulating the left side of the heart. Re-synchronization of the pumping function in a failing heart can be obtained by stimulating both the right and left side of the heart. Electrode systems of the type used with the present invention are well known to those skilled in the relevant arts.

One example of such a standard electrode array is described in U.S. Pat. No. 6,993,379 B1, issued Jan. 31, 2006, and commonly owned with the present invention. The disclosure of the '379 patent is incorporated herein in its entirety as though set forth in full below. In this embodiment, sensor 104 comprises part of a pacing electrode implanted in a coronary vein. Alternatively, sensor 104 can be separate from a standard electrode array. Sensor 104 is coupled to an input of a sensor interface 106, which generates an output which is a raw unprocessed sensor signal Sig 1. Signal Sig 1 is applied as an input to a signal processing block 108. Signal processing block 108 is described in more detail in FIG. 2 below. The output Sig 5 of signal processing block 108 is provided as one input to an event detection block 109.

Sensor interface 106 provides signal conditioning to obtain an electrical representation of the sensed mechanical activity. Sensor interface output Sig 1 preferably delivers a stream of sampled digital values. An analog to digital converter in interface 106 converts the measured analog signal to digital signals for further processing. A typical sampling frequency is 100-1000 Hz giving 100-1000 values per second in the data stream (Sig 1). Alternatively, the A/D-converted value may be stored in a data buffer (memory). A buffer containing 10K locations can store 10 s of streamed data at 1 KHz for later processing.

The measurement of electrical events in the heart, for instance a spontaneous R-wave in the right ventricle, is often combined with continuous electrical impedance measurements between different nodes in the electrode system. The already implanted electrodes are used for that so no special electrodes need to be implanted in the patient. An example is to measure the impedance between the tip and ring of an electrode implanted in the right ventricle. This will give a measure of the heart's ability to contract or the blood volume in the right ventricle. Another example is to measure the impedance over the lungs in order to sense the respiration minute volume. The pacemaker housing is often one of the nodes in this case. The last is an example of a metabolic sensor.

The output of signal processing block 108 is a processed sensor signal, Sig 5, which is suitable for detection of the time events aortic valve opening and aortic valve closing. PEP is determined as the time interval between electrical activation and aortic valve opening. EMS is determined as the time interval between electrical activation and aortic valve closing. The ejection time (ET) is the time difference EMS–PEP. The detection of PEP and EMS is defined to occur within two predefined time-windows, TW1 and TW2, within a heart beat, as discussed in more detail below with particular reference to FIG. 7.

System 100 also includes a metabolic sensor 110, a posture sensor 112, and a telemetry block 114. Sensor 110 measures the respiration minute volume, which typically increases during physical work and can be used to control the stimulation rate in the pacemaker. Posture sensor 112 (see, for instance, U.S. Pat. No. 6,044,297) further increases the ability of the implantable device to deliver better therapy or diagnostics. It is known that the body position affects, for instance, the impedance morphology.

Sensors 110 and 112 are coupled to pulse generator 102 and can be used together with the heart rate to put constraints on when the measurement of PEP and ET should be performed. For example the measurement can be performed during V00 pacing at 80 PPM when the patient is resting in bed.

A telemetry block 114 handles the data communication with an external device, such as a programmer. Parameter settings for controlling the therapy can be transferred to the implanted device from the programmer. Real time data and stored diagnostics can be transferred from the device to the programmer. Techniques for setting parameters in the implanted device and for transferring data from the device to an external collector are well known to those skilled in the relevant arts.

Figure 2:
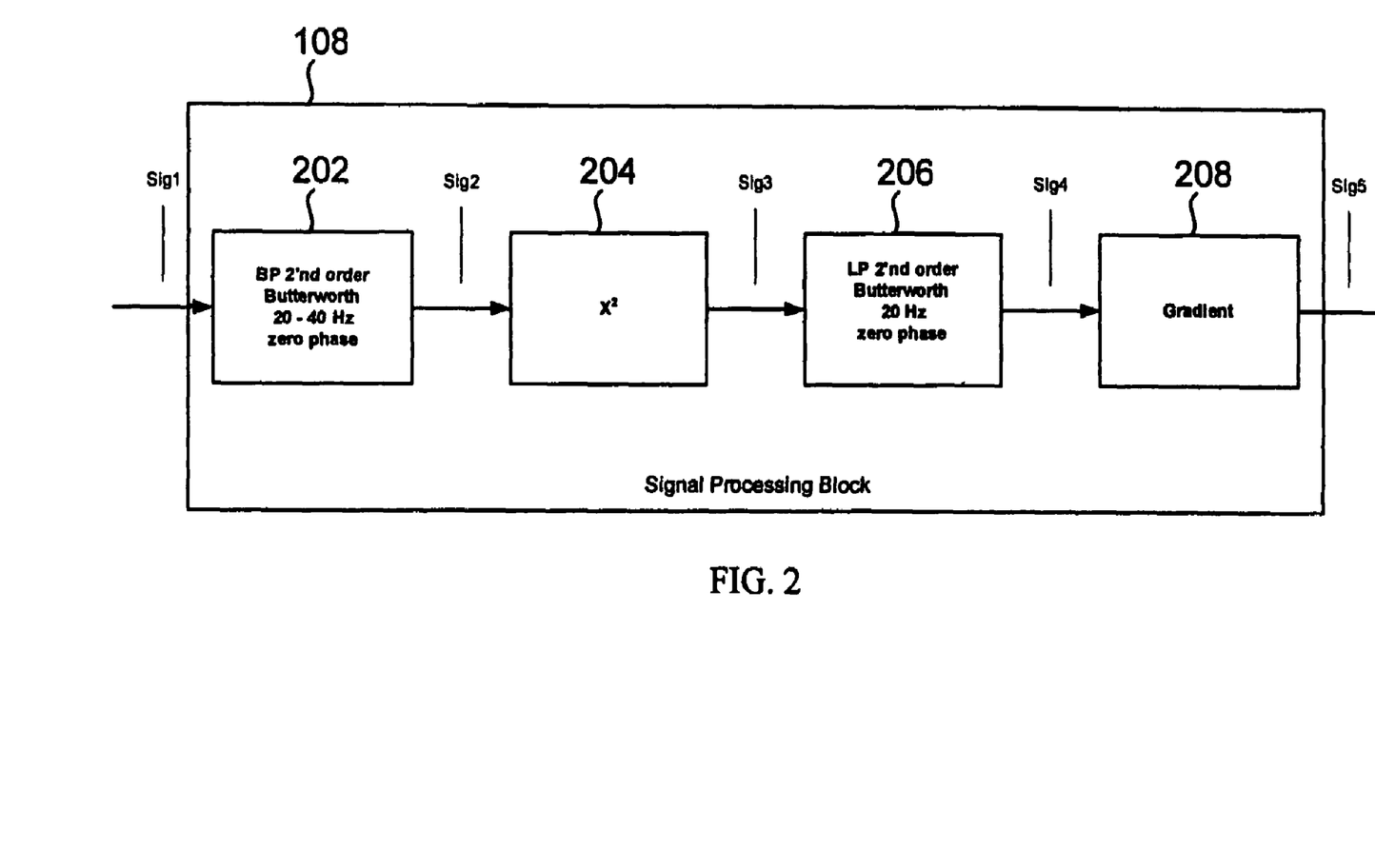
FIG. 2 shows details of the signal processing block in FIG. 1.

FIG. 2 shows details of signal processing block 108. Block 108 includes a first second order Butterworth filter 202. The output signal Sig 2 of filter 202 is applied to a non-linear block 204 for squaring the sample values. The squared output, Sig 3, represents the power of the input Sig 2. The output of non-linear block 204 is provided to a second Butterworth filter 206, which generates an output signal Sig 4. A gradient block 208 calculates the time derivative of smoothed power Sig 4 by differencing the output from the second zero phase Butterworth filter 206 to provide an output signal Sig 5.

In one example, input signal Sig 1 is sampled at more than 100 Hz and then is first band pass filtered to cut out the frequency band 20-40 Hz. The resultant signal Sig 2 is then squared. The resulting signal Sig 3 represents the instantaneous power of Sig 2. A smoothing low pass filter is then applied to obtain signal Sig 4 before the gradient is calculated to provide output signal Sig 5.

This signal processing chain allows robust and morphology independent detection of the time events PEP and EMS. It is also understood that modifications of the proposed filter frequencies are allowed. For instance the input zero phase Butterworth filter cut-off can be set to 18 Hz-42 Hz.

Figure 3:
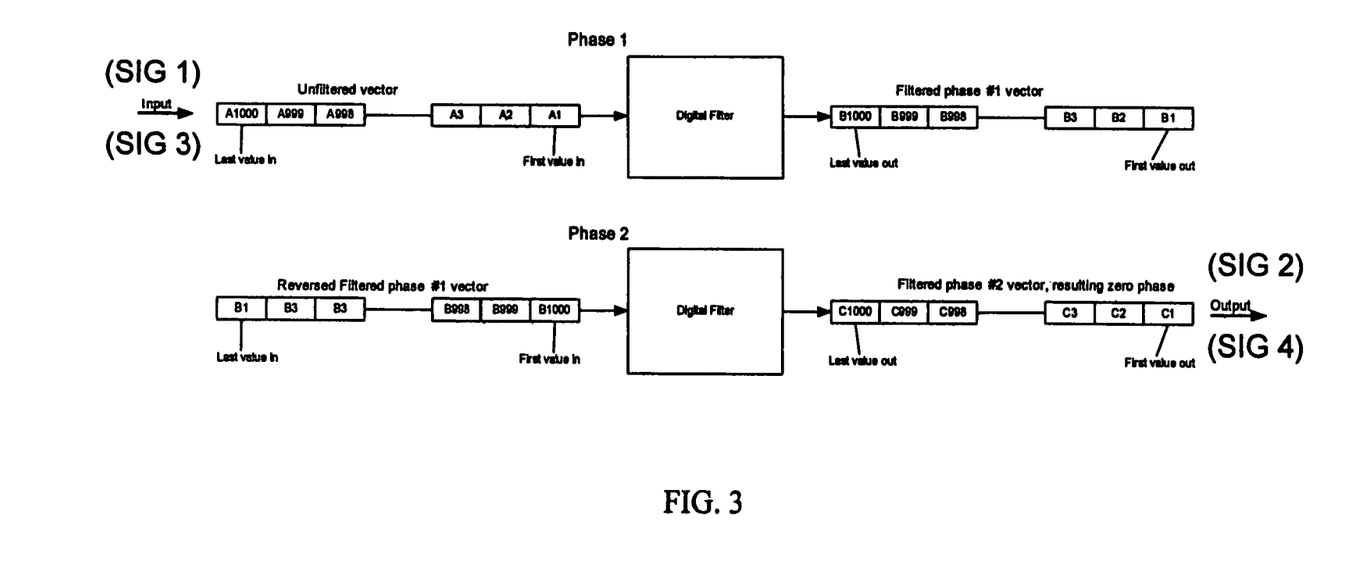
FIG. 3 shows details of the filters used in the signal processing block of FIG. 2.

FIG. 3 shows details of Butterworth filters 202 and 206. The Input and Output is represented by Sig 1 and Sig 2 for the first filter 202 and Sig 3 and Sig 4 represent the corresponding inputs and outputs for the second filter 206. A special two-phase filtering technique is used to achieve a zero delay (phase) in the filtered signals. Data buffering is used to store the intermediate results. The example shows filtering of 1000 buffered values.

Phase #1 uses conventional forward filtering. The unfiltered values A1 to A1000 are filtered by the digital filter resulting in the intermediate values B1 to B1000 (in this order). The order of B1 to B1000 is then reversed before the second time filtering by the same digital filter. The resulting values C1 to C1000 are a zero delayed filtered version of the input vector A1 to A1000. It contains the cut-out frequency range with no time-shift in the signal morphology. Between the two filtering blocks is a non-linear block, a squaring of the sample values. The squaring means that the output signal Sig 3 represents the power of the input signal Sig 2.

Figure 4:
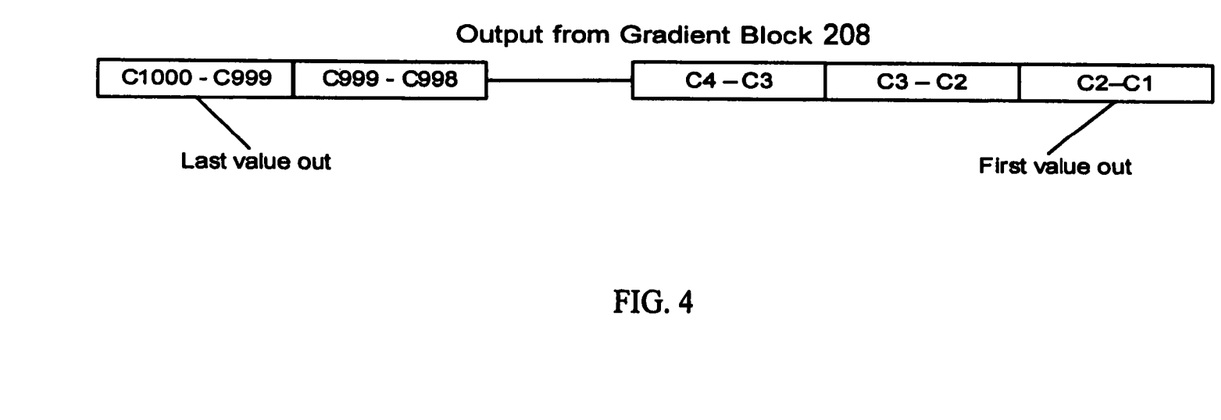
FIG. 4 shows a detail of the gradient block used in the signal processing block of FIG. 2.

FIG. 4 shows a detail of the gradient block 208. Gradient block 208 calculates the derivative of smoothed power Sig 4 by differencing the output from the second zero phase filter to obtain output signal Sig 5.

Figure 5:
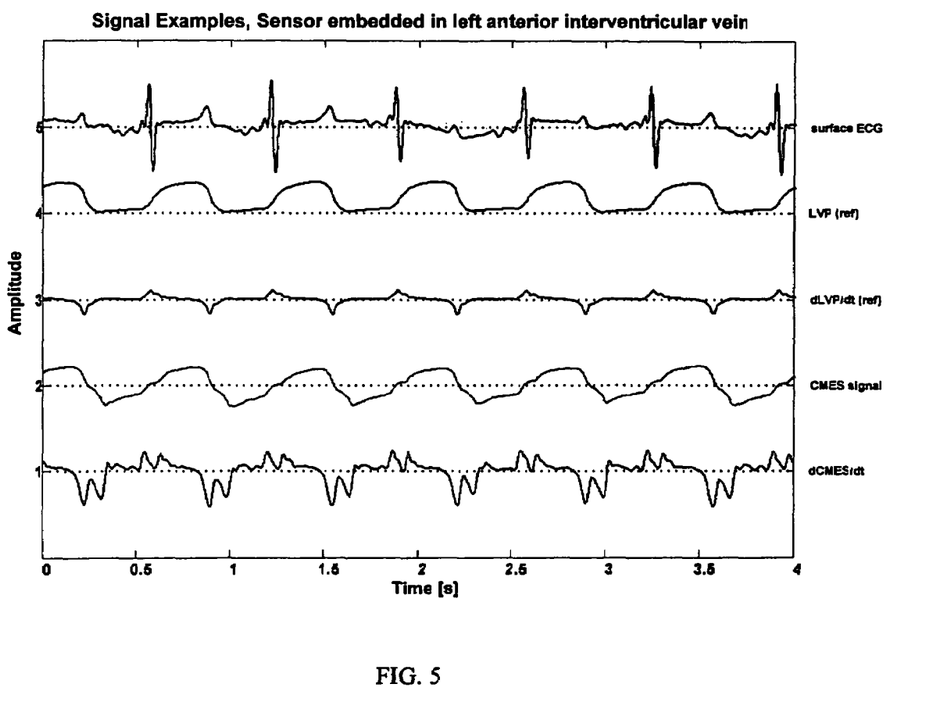
FIG. 5 is a chart showing signal examples for a sensor embedded in the left anterior interventricular vein.

FIG. 5 is a chart showing signal examples where a sensor is embedded in the left anterior interventricular vein. In the chart from top to bottom, trace No. 5 is a surface ECG showing electrical events. Trace No. 4 shows left ventricular pressure (LVP)—high fidelity reference pressure sensor in the left ventricle. Trace No. 3 shows dLVP/dt—the time derivative of reference pressure sensor. Trace No. 2 shows the CMES— sensor located in a coronary vein and pressure like in this case. Trace No. 1 shows dCMES/dt—the time derivative showing split first and second peaks, which is input to the processing chain.

Figure 6:
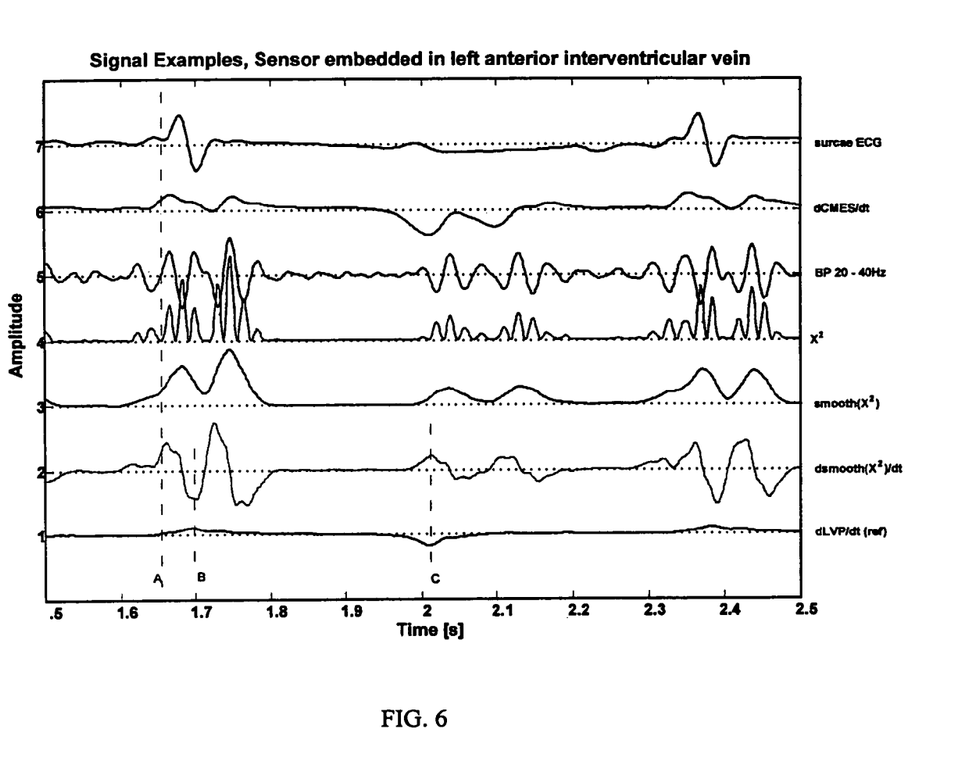
FIG. 6 is another chart showing additional signal examples for a sensor embedded in the left anterior interventricular vein.

FIG. 6 is a chart showing further signal examples where a sensor is embedded in the left anterior interventricular vein. In the chart, from top to bottom, Trace No. 7 is a surface ECG showing electrical events. Trace No. 6 is dCMES/dt—the time derivative showing split first and second peaks—input to processing chain. Trace No. 5 is a bandpass filtered time derivative. Trace No. 4 is the power of the bandpass filtered time derivative. Trace No. 3 is the smoothed power. Trace No. 2 is the derivative of smoothed power—used for finding aortic valve events. Trace No. 1 is the dLVP/dt—time derivative of reference pressure sensor.

Referring to FIG. 6, time 1.6-1.8 s, is the split first peak and split time derivative. Time 1.95-2.2 s, is the split second peak and split time derivative. Time A is the onset of electrical activation. Time B is the first minimum peak in a first time window (typical 10-180 ms) of the processed time derivative coincident with the positive peak of dVLP/dt—aortic valve opening. Time C is the first maximum peak in a second time window (typical 190-500 ms) of the processed time derivative coincident with the negative peak of dVLP/dt—aortic valve closing.

$$PEP=T(B)-T(A)=44 \text{ ms}$$

$$LVET=T(C)-T(B)=315 \text{ ms}$$

which gives in this case:

$$EMS=PEP+LVET=359 \text{ ms}$$

STR=PEP/LVET=0.14 and >0.35, higher than normal contractility

EF=75% using Capan's formula

Figure 7:
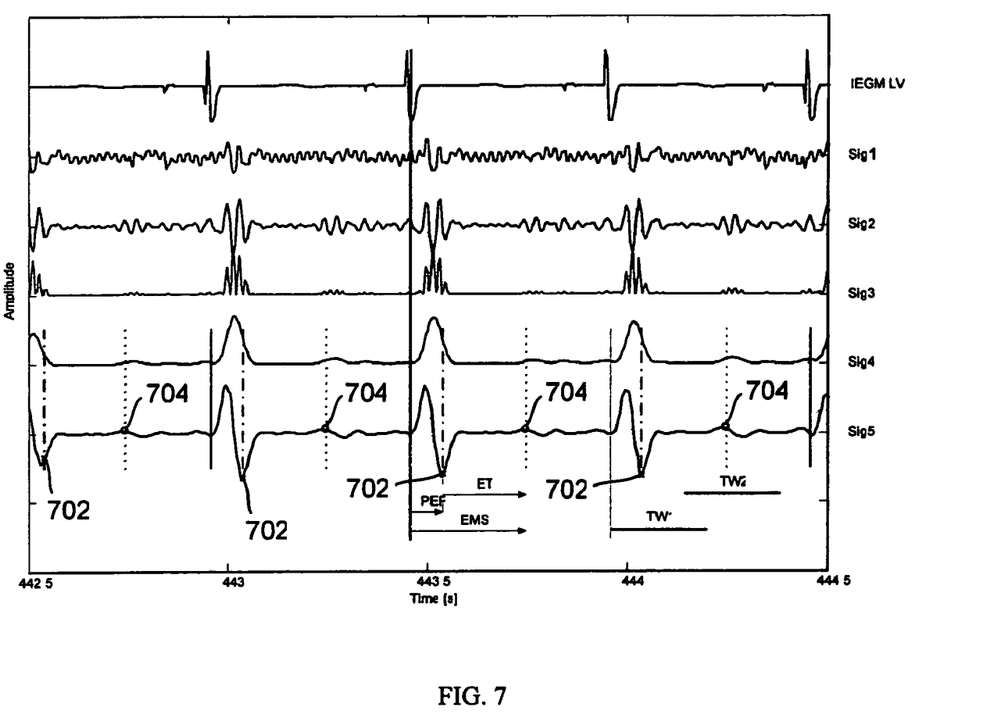
FIG. 7 shows signal examples correlating with the signal processing block of FIG. 2.

FIG. 7 shows the following signal examples correlating with the signal processing block 108:

IEGM LV—a left side IEGM, showing the electrical activity of the heart.

Sig 1—represents the time derivative of the raw unprocessed sensor signal measured in a left side coronary vein. The signal is heavily corrupted by noise in this case.

Sig 2—the band pass filtered signal.

Sig 3—the instantaneous power of Sig 2.

Sig 4—the smoothed instantaneous power of Sig 2.

Sig 5—the rate of change (time derivative) of the smoothed instantaneous power of Sig 2, input to event detection block 109.

Time events are also marked with lines as follows:

Solid line: Detected QRS.

Dash dot: Opening of the aorta valve obtained by a reference pressure sensor.

Dotted: Closing of the aortic valve obtained by a reference pressure sensor.

It can be seen that the opening and closing of the aortic valve coincide with a large minimum 702 and a lower local maximum 704. The detection windows TW1 and TW2 are marked in the next heart beat.

For example, time window TW1, used for the detection of PEP, starts 10 ms after a detected spontaneous QRS or a delivered stimulation pulse in the ventricle and ends after 250 ms. Time-window TW2, used for the detection of EMS, starts 200 ms after a detected spontaneous QRS or a delivered stimulation pulse in the ventricle and ends after 400 ms. Those fixed time points can also be set as a fraction of the heart beat interval. It is understood that the value of EMS is larger than the PEP value (EMS>PEP) for acceptance.

The function of event detection block 109 is to find those local extremes.

The measured PEP, EMS and LVET (systolic time intervals, STI) can be used for diagnostic purposes or to control the therapy.

LVET is the left ventricular ejection time.

From the literature:

PLR=PEP/LVET RATIO: (PEP/LVET RATIO=PLR), also known as STR (SYSTOLIC TIME RATIO)

PEP=Pre-ejection time

LVET=Left Ventricular Ejection Time

PEP/LVET RATIO is the ratio that expresses contractility in an inverse fashion. Thus the PEP to LVET ratio increases in magnitude as contractility diminishes. (Normal value for humans is about 0.35.)

PLR is inversely proportional to contractility.

Weissler et al derived the index (PEP/LVET) which was less heart rate dependent as a measure of LV systolic function:

Ejection Fraction from timing relation:

EF=1.125−1.25*(PEP/LVET), (from Garrad C L, Weissler A M, Dodge HT. Circulation 1970; 42: 455-462.)  Formula 1

EF=0.84−0.64*(PEP/LVET), (from Capan L V, Bernstein D P, Patel KP et al. Crit Med 1987; 15: 402)  Formula 2

It can be observed that the general expression is

EF=$A-B$*(PEP/LVET), where A and B are two positive constants.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for measuring ejection fraction in a mammalian heart, comprising the steps of:
    sensing opening and closing of a heart valve in the heart of a mammalian subject, and generating a sensor signal representing said opening and closing of said heart valve, said heart exhibiting a heartbeat rate;
    filtering said sensor signal to extract a signal component therefrom, as a filtered signal, in a frequency range much higher than said heartbeat rate;
    squaring said filtered signal to obtain a power signal representing power of said filtered signal;
    providing said power signal to an electronic detection unit and, in said electronic detection unit, measuring, in said power signal, a pre-ejection period of said heart as a function of the sensed opening and closing of said heart valve;
    additionally in said electronic detection unit, measuring, in said power signal, a ventricular ejection time of said heart;
    in said electronic detection unit, automatically determining an ejection fraction of the heart as a function of the measured pre-ejection period and the measured ventricular ejection time; and
    emitting an electronic output signal from said electronic detection unit representing said ejection function.

2. A method as claimed in claim 1 wherein the step of filtering said sensor signal comprises bandpass filtering said sensor signal to extract a signal component therefrom in a frequency range between approximately 20 and 40 Hz.

3. A method as claimed in claim 1 comprising bandpass filtering said sensor signal in a frequency range between 18 and 42 Hz.

4. A method as claimed in claim 1 comprising filtering said sensor signal in a second order, zero phase Butterworth filter.

5. A method as claimed in claim 1 wherein the step of filtering said sensor signal comprises:
    filtering said sensor signal in a first filter to extract a signal component therefrom, as a first filtered signal, in said frequency range substantially higher than said heartbeat rate;
    squaring said first filtered signal to obtain a squared signal;
    filtering said squared signal in a second filter to obtain a second filtered signal;
    differentiating said second filtered signal to obtain a first derivative with respect to time of said second filtered signal; and
    providing said first derivative to said electronic detection unit as said power signal.

6. A method as claimed in claim 5 comprising employing a bandpass, second order, zero phase Butterworth filter as said first filter, and employing a low-pass, second order, zero phase Butterworth filter as said second filter.

7. A method as claimed in claim 1 comprising sampling said sensor signal before filtering said sensor signal.

8. A method as claimed in claim 1 comprising:
    in said electronic detection unit, measuring the pre-ejection period a plurality of times during a predetermined time period;
    in said electronic detection unit, measuring the ventricular ejection time said plurality of times during said predetermined time period;
    in said electronic detection unit, determining the ejection fraction said plurality of times during said predetermined time period, to obtain a plurality of ejection fraction determinations that are represented in said output signal; and
    supplying said output signal to a memory and storing said plurality of determined ejection fractions in said memory.

9. A method as claimed in claim 8 comprising reading out said plurality of determined ejection fractions from said memory from a location remote from said memory and said electronic detection unit.

10. A method as claimed in claim 1 comprising supplying said output signal to a therapy administration unit configured to interact with said mammalian subject to administer medical therapy to said mammalian subject, and automatically controlling administration of said medical therapy by said therapy administration unit dependent on the ejection fraction represented in said output signal.

11. An apparatus for measuring ejection fraction in a mammalian heart, comprising:
    a sensor configured to sense opening and closing of a heart valve in the heart of a mammalian subject, and to generate a sensor signal representing said opening and closing of said heart valve, said heart exhibiting a heartbeat rate;
    a filter supplied with said sensor signal that extracts a signal component therefrom, as a filtered signal, in a frequency range much higher than said heartbeat rate;
    a squaring unit supplied with said filtered signal that squares said filtered signal to obtain a power signal; and
    an electronic detection unit supplied with said power signal, said electronic detection unit being configured to measure, in said power signal, a pre-ejection period of said heart as a function of the sensed opening and closing of said heart valve, and to measure, in said power signal, a ventricular ejection time of said heart, and to automatically determine an ejection fraction of the heart as a function of the measured pre-ejection period and the measured ventricular ejection time, and to emit an electronic output signal representing said ejection function.

12. An apparatus as claimed in claim 11 wherein said filter is a bandpass filter that filters said sensor signal to extract a signal component therefrom in a frequency range between approximately 20 and 40 Hz.

13. An apparatus as claimed in claim 11 wherein said bandpass filtering filter passes said sensor signal in a frequency range between 18 and 42 Hz.

14. An apparatus as claimed in claim 11 wherein said filter is a second order, zero phase Butterworth filter.

15. An apparatus as claimed in claim 11 wherein said filter is a first filter that produces a first filtered signal, and comprising:
- said squaring unit squaring said first filtered signal to obtain a squared signal;
- a second filter that filters said squared signal to obtain a second filtered signal;
- a differentiator that differentiates said second filtered signal to obtain a first derivative with respect to time of said second filtered signal and that provides said first derivative to said electronic detection unit as said power signal.

16. An apparatus as claimed in claim 15 wherein said first filter is a bandpass, second order, zero phase Butterworth filter, and said second filter is a low-pass, second order, zero phase Butterworth filter.

17. An apparatus as claimed in claim 11 comprising a sampling unit that samples said sensor signal before filtering said sensor signal in said filter.

18. An apparatus as claimed in claim 11 wherein said electronic detection unit is configured to measure the pre-ejection period a plurality of times during a predetermined time period, and to measure the ventricular ejection time said plurality of times during said predetermined time period, and to determine the ejection fraction said plurality of times during said predetermined time period, to obtain a plurality of ejection fraction determinations that are represented in said output signal, and wherein said apparatus comprises a memory supplied with said output signal to store said plurality of determined ejection fractions in said memory.

19. An apparatus as claimed in claim 18 comprising a telemetry unit configured to allow readout of said plurality of determined ejection fractions from said memory from a location remote from said memory and said electronic detection unit.

20. An apparatus as claimed in claim 11 comprising a therapy administration unit configured to interact with said mammalian subject to administer medical therapy to said mammalian subject, said therapy administration unit being supplied with said output signal and automatically controlling administration of said medical therapy dependent on the ejection fraction represented in said output signal.

* * * * *